United States Patent
Kai et al.

(10) Patent No.: US 9,343,685 B2
(45) Date of Patent: *May 17, 2016

(54) ORGANIC ELECTROLUMINESCENT ELEMENT

(75) Inventors: Takahiro Kai, Kitakyushu (JP); Masaki Komori, Kitakyushu (JP); Toshihiro Yamamoto, Kitakyushu (JP); Tohru Asari, Kitakyushu (JP); Takaya Ishiyama, Kitakyushu (JP); Megumi Matsumoto, Kitakyushu (JP)

(73) Assignee: NIPPON STEEL & SUMIKIN CHEMICAL CO., LTD., Tokyo (JP)

(*) Notice: Subject to any disclaimer, the term of this patent is extended or adjusted under 35 U.S.C. 154(b) by 433 days.

This patent is subject to a terminal disclaimer.

(21) Appl. No.: 13/881,715

(22) PCT Filed: Nov. 21, 2011

(86) PCT No.: PCT/JP2011/076772
§ 371 (c)(1),
(2), (4) Date: Apr. 25, 2013

(87) PCT Pub. No.: WO2012/070519
PCT Pub. Date: May 31, 2012

(65) Prior Publication Data
US 2013/0207097 A1 Aug. 15, 2013

(30) Foreign Application Priority Data
Nov. 25, 2010 (JP) .................. 2010-262167

(51) Int. Cl.
| H01L 51/54 | (2006.01) |
| C09K 11/06 | (2006.01) |
| H01L 51/00 | (2006.01) |
| C07D 487/04 | (2006.01) |
| H05B 33/14 | (2006.01) |
| C07D 487/22 | (2006.01) |
| H01L 51/50 | (2006.01) |

(52) U.S. Cl.
CPC .......... *H01L 51/0072* (2013.01); *C07D 487/04* (2013.01); *C07D 487/22* (2013.01); *C09K 11/06* (2013.01); *H01L 51/0067* (2013.01); *H05B 33/14* (2013.01); *C09K 2211/1007* (2013.01); *C09K 2211/1022* (2013.01); *C09K 2211/1029* (2013.01); *C09K 2211/1044* (2013.01); *C09K 2211/1059* (2013.01); *C09K 2211/1092* (2013.01); *H01L 51/0085* (2013.01); *H01L 51/5016* (2013.01); *H01L 51/5056* (2013.01); *H01L 51/5072* (2013.01); *H01L 51/5096* (2013.01)

(58) Field of Classification Search
None
See application file for complete search history.

(56) References Cited

U.S. PATENT DOCUMENTS

| 8,389,131 B2 * | 3/2013 | Kai et al. .................. 428/690 |
| 2010/0187977 A1 | 7/2010 | Kai et al. |
| 2011/0037062 A1 | 2/2011 | Fukumatsu et al. |
| 2011/0315975 A1 | 12/2011 | Kai et al. |
| 2012/0153272 A1 | 6/2012 | Fukuzaki |

FOREIGN PATENT DOCUMENTS

| WO | WO 2010113726 A1 * | 10/2010 |
| WO | WO 2011025018 A1 * | 3/2011 |

OTHER PUBLICATIONS

International Search Report for the Application No. PCT/JP2011/076772 mailed Feb. 14, 2012.

* cited by examiner

*Primary Examiner* — Andrew K Bohaty
(74) *Attorney, Agent, or Firm* — Cheng Law Group, PLLC

(57) ABSTRACT

Provided is an organic electroluminescent device (EL device) that uses an indolocarbazole compound. The organic EL device includes an anode, a plurality of organic layers including a phosphorescent light-emitting layer, and a cathode laminated on a substrate, in which at least one organic layer selected from the phosphorescent light-emitting layer, a hole-transporting layer, an electron-transporting layer, and a hole-blocking layer contains an indolocarbazole compound represented by the general formula (1). In the general formula (1), a ring I and a ring II represent rings represented by the formula (1a) and the formula (1b), respectively, each of which are fused to an adjacent ring. X's each represent nitrogen or C—Y and at least one of X's represents nitrogen. Y's each represent hydrogen, an alkyl group, a cycloalkyl group, or an aromatic group. A represents an alkyl group, a cycloalkyl group, or an aromatic group. At least one of Y and A represents an alkyl group or a cycloalkyl group. R's each represent hydrogen, an alkyl group, a cycloalkyl group, an aromatic hydrocarbon group, or an aromatic heterocyclic group.

6 Claims, 1 Drawing Sheet

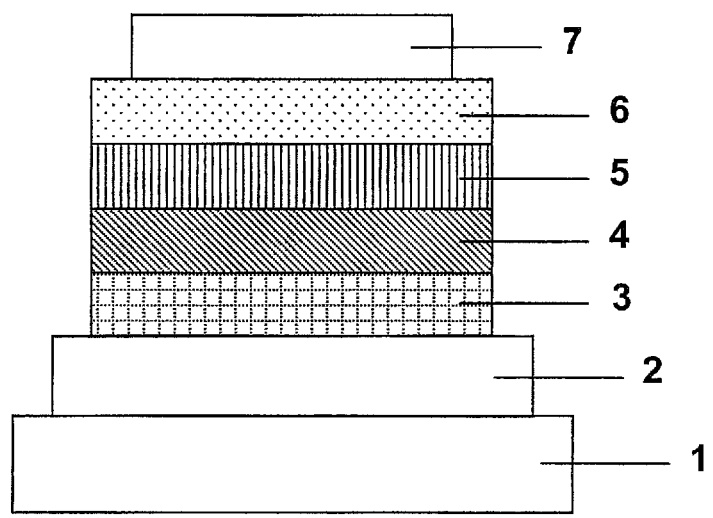

ORGANIC ELECTROLUMINESCENT ELEMENT

TECHNICAL FIELD

The present invention relates to an organic electroluminescent device containing an indolocarbazole compound, and more specifically, to a thin-film-type device that emits light when an electric field is applied to a light-emitting layer formed of an organic compound.

BACKGROUND ART

In general, an organic electroluminescent device (hereinafter referred to as organic EL device) is constructed of a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer formed of an 8-hydroxyquinoline aluminum complex (hereinafter referred to as Alq3) are provided between electrodes as thin films, resulting in a significant improvement in luminous efficiency, compared with conventional devices in which a single crystal of anthracene molecules or the like is used. Thus, the development of the above-mentioned organic EL device has been promoted in order to accomplish its practical application to a high-performance flat panel having features such as self-luminescence and rapid response.

Further, studies have been made on using phosphorescent light rather than fluorescent light as an attempt to raise the luminous efficiency of a device. Many kinds of devices including the above-mentioned device in which a hole-transporting layer formed of an aromatic diamine and a light-emitting layer formed of Alq3 are provided emit light by using fluorescent light emission. However, by using phosphorescent light emission, that is, by using light emission from a triplet excited state, luminous efficiency is expected to be improved by about three times to four times, compared with the case of using conventional devices in which fluorescent light (singlet) is used. In order to accomplish this purpose, studies have been made on adopting a coumarin derivative or a benzophenone derivative as a light-emitting layer, but extremely low luminance has only been provided. Further, studies have been made on using a europium complex as an attempt to use a triplet state, but highly efficient light emission has not been accomplished. In recent years, many studies on a phosphorescent light-emitting dopant material centered on an organic metal complex such as an iridium complex have been made, as described in Patent Literature 1, for the purpose of attaining the high efficiency and long lifetime of light emission.

CITATION LIST

Patent Literature

[PTL 1] JP 2003-515897 T
[PTL 2] JP 2001-313178 A
[PTL 3] JP 11-162650 A
[PTL 4] JP 11-176578 A
[PTL 5] WO 2008/056746 A1

In order to obtain high luminous efficiency, host materials that are used with the dopant materials described above play an important role. Typical examples of the host materials proposed include 4,4'-bis(9-carbazolyl)biphenyl (hereinafter referred to as CBP) as a carbazole compound disclosed in Patent Literature 2. When CBP is used as a host material for a green phosphorescent light-emitting material typified by a tris(2-phenylpyridine)iridium complex (hereinafter referred to as Ir(ppy)$_3$), the injection balance between charges is disturbed because CBP has the characteristic of facilitating the delivery of holes and not facilitating the delivery of electrons. Thus, excessively delivered holes flow out into an electron-transporting layer side, with the result that the luminous efficiency from Ir(ppy)$_3$ lowers.

In order to provide high luminous efficiency to an organic EL device as described above, it is necessary to use a host material, which has high triplet excitation energy, and is striking a good balance in both charge (hole and electron)-injecting/transporting property. Further desired is a compound, which has electrochemical stability, has high heat resistance, and has excellent amorphous stability, and hence further improvement has been demanded.

Patent Literature 3 discloses the indolocarbazole compound shown below as a hole-transporting material.

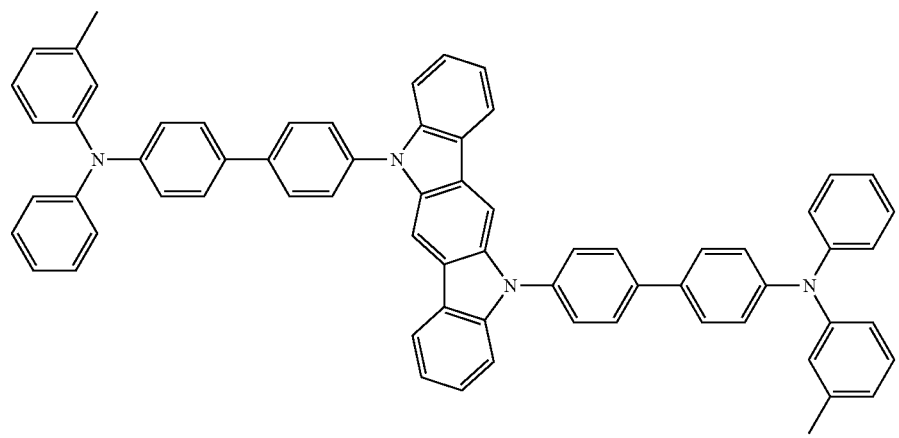 [SMILES: Cc1cccc(N(c2ccccc2)c2ccc(-c3ccc(-n4c5ccccc5c5cc6c(cc54)c4ccccc4n6-c4ccc(-c5ccc(N(c6ccccc6)c6cccc(C)c6)cc5)cc4)cc3)cc2)c1]

Patent Literature 4 discloses the indolocarbazole compound shown below as a hole-transporting material.

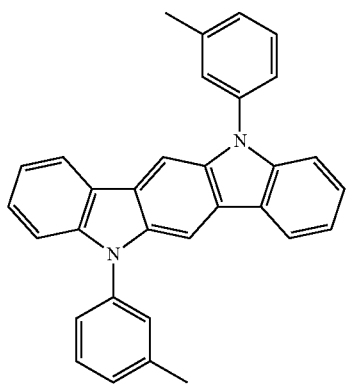 [SMILES: Cc1cccc(-n2c3ccccc3c3cc4c(cc32)c2ccccc2n4-c2cccc(C)c2)c1]

However, although the literature recommends to use these compounds having an indolocarbazole skeleton as hole-transporting materials, the literature only discloses examples of using each compound in a fluorescent light-emitting device, and does not disclose the use of the compounds as materials for a phosphorescent light-emitting device.

Patent Literature 5 discloses such an indolocarbazole compound as shown below as a host material, and discloses that an organic EL device using the compound is improved in luminous efficiency and has high driving stability.

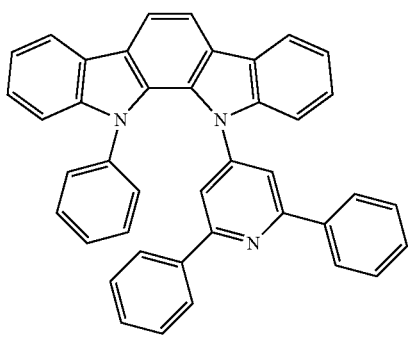 [SMILES: c1ccc(-c2cc(-n3c4ccccc4c4ccc5c6ccccc6n(-c6ccccc6)c5c43)cc(-c3ccccc3)n2)cc1]

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device, which has high efficiency, has high driving stability, and is practically useful and a compound suitable for the organic EL device.

The inventors of the present invention have made intensive studies and have consequently found that, when a compound having an indolocarbazole skeleton with a specific structure is used in an organic EL device, the organic EL device exhibits excellent characteristics. As a result, the present invention has been completed.

The present invention relates to an organic electroluminescent device, including an anode, a plurality of organic layers including a phosphorescent light-emitting layer, and a cathode laminated on a substrate, in which at least one organic layer selected from the group consisting of the phosphorescent light-emitting layer, a hole-transporting layer, an electron-transporting layer, and a hole-blocking layer contains an indolocarbazole compound represented by the following general formula (1).

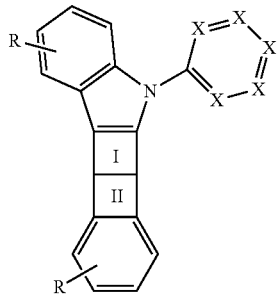

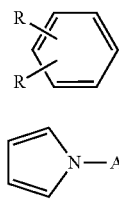

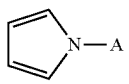

In the formula (1), a ring I represents an aromatic hydrocarbon ring represented by the formula (1a) that is fused to an adjacent ring at arbitrary positions, a ring II represents a heterocycle represented by the formula (1b) that is fused to an adjacent ring at arbitrary positions, X's each independently represent nitrogen or C—Y and at least one of X's represents nitrogen, and Y's each independently represent hydrogen, an alkyl group having 1 to 10 carbon atoms, a cycloalkyl group having 3 to 11 carbon atoms, an aromatic hydrocarbon group having 6 to 12 carbon atoms, or an aromatic heterocyclic group having 3 to 12 carbon atoms, in the formula (1b), A represents an alkyl group having 1 to 10 carbon atoms, a cycloalkyl group having 3 to 11 carbon atoms, an aromatic hydrocarbon group having 6 to 30 carbon atoms, or an aromatic heterocyclic group having 3 to 30 carbon atoms and free of a fused heterocycle having 5 or more rings, provided that at least one of Y and A represents an alkyl group having 1 to 10 carbon atoms or a cycloalkyl group having 3 to 11 carbon atoms, and in the general formula (1) and the formula (1a), R's each independently represent hydrogen, an alkyl group having 1 to 10 carbon atoms, a cycloalkyl group having 3 to 11 carbon atoms, an aromatic hydrocarbon group having 6 to 12 carbon atoms, or an aromatic heterocyclic group having 3 to 12 carbon atoms.

Of the indolocarbazole compounds each represented by the general formula (1), an indolocarbazole compound represented by the following general formula (2) is given as a preferred compound.

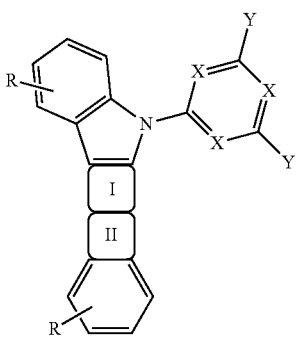

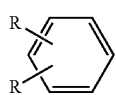

(1a)

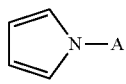

(1b)

In the general formula (2), a ring I, a ring II, A, Y's, and R's have the same meanings as those in the general formula (1), and X's each independently represent nitrogen or CH and at least one of X's represents nitrogen, provided that at least one of Y's represents an alkyl group having 1 to 10 carbons or a cycloalkyl group having 3 to 11 carbon atoms.

Of the indolocarbazole compounds each represented by the general formula (2), an indolocarbazole compound represented by any one of the following general formulae (3) to (6) is given as a more preferred compound.

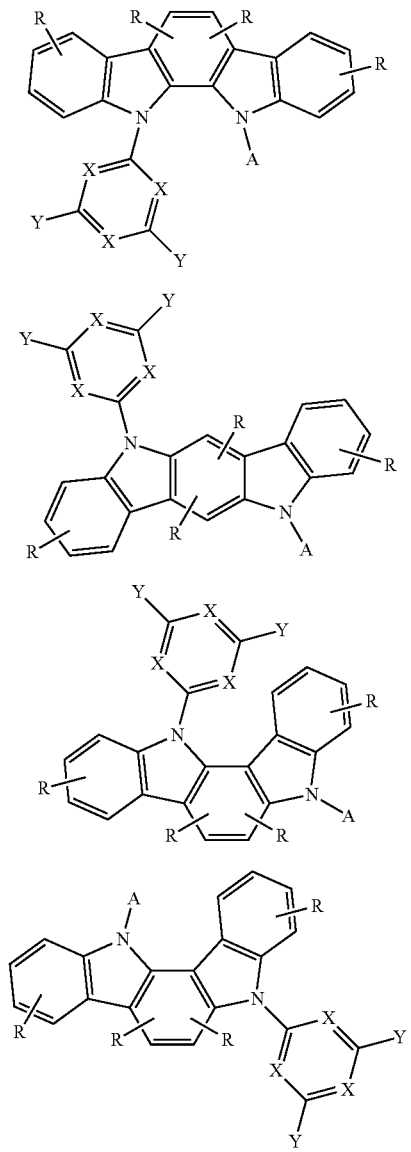

(3)

(4)

(5)

(6)

In the general formulae (3) to (6), A's and R's have the same meanings as those in the general formula (1), and X's and Y's have the same meanings as those in the general formula (2).

Further, it is preferred that the organic electroluminescent device include a light-emitting layer containing the indolocarbazole compound and a phosphorescent light-emitting dopant.

BRIEF DESCRIPTION OF DRAWINGS

FIG. 1 is a sectional view illustrating an example of the structure of an organic EL device.

DESCRIPTION OF EMBODIMENTS

An organic electroluminescent device of the present invention contains an indolocarbazole compound represented by the general formula (1) (hereinafter sometimes referred to as "compound represented by the general formula (1)" or "indolocarbazole compound").

In the general formula (1), a ring I represents an aromatic hydrocarbon ring represented by the formula (1a) that is fused to an adjacent ring at arbitrary positions, and a ring II represents a heterocycle represented by the formula (1b) that is fused to an adjacent ring at arbitrary positions.

In the indolocarbazole skeleton represented by the general formula (1), the aromatic hydrocarbon ring represented by the formula (1a) may be fused with two adjacent rings at arbitrary positions, but there is a position at which the aromatic hydrocarbon ring cannot be fused with the rings from the structural viewpoint. The aromatic hydrocarbon ring represented by the formula (1a) has six sides, and is not fused with the two adjacent rings through two adjacent sides. Further, the heterocycle represented by the formula (1b) may be fused with two adjacent rings at arbitrary positions, but there is a position at which the heterocycle cannot be fused with the rings from the structural viewpoint. That is, the heterocycle represented by the formula (1b) has five sides, and is not fused with the two adjacent rings through two adjacent sides and is not fused with an adjacent ring through a side including a nitrogen atom. Thus, there is a limitation on the kind of the indolocarbazole skeleton.

In the general formula (1), the indolocarbazole skeleton is preferably represented by any one of the following forms. Preferred fusion positions of the aromatic hydrocarbon ring and the heterocycle in the indolocarbazole skeleton are understood from these examples.

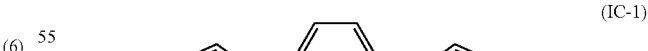

(IC-1)

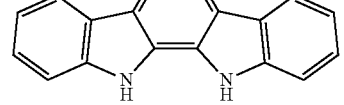

(IC-2)

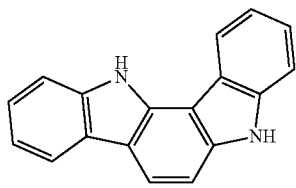
(IC-3)

In the general formula (1), X's each independently represent nitrogen or C—Y and at least one of X's represents nitrogen. It is preferred that one to four of X's each represent nitrogen, and it is more preferred that one to three of X's each represent nitrogen.

Y's each independently represent hydrogen, an alkyl group having 1 to 10 carbon atoms, a cycloalkyl group having 3 to 11 carbon atoms, an aromatic hydrocarbon group having 6 to 12 carbon atoms, or an aromatic heterocyclic group having 3 to 12 carbon atoms. Y's each preferably represent hydrogen, an alkyl group having 1 to 10 carbon atoms, or a cycloalkyl group having 3 to 11 carbon atoms, and each more preferably represent an alkyl group having 1 to 8 carbon atoms or a cycloalkyl group having 5 to 6 carbon atoms.

It is preferred that in the six-membered ring group including X's of the general formula (1), X's at its 3- and 5-positions each represent C—Y, X's at its 2-, 4-, and 6-positions each represent nitrogen or CH, and at least one of X's represent nitrogen. In addition, at least one Y preferably represents an alkyl group having 1 to 10 carbon atoms or a cycloalkyl group having 3 to 11 carbon atoms. In addition, A of the formula (1b) preferably represents an aromatic hydrocarbon group having 6 to 30 carbon atoms, or an aromatic heterocyclic group having 3 to 30 carbon atoms and free of a fused heterocycle having 5 or more rings.

Specific examples of the alkyl group include a methyl group, an ethyl group, a propyl group, a butyl group, a pentyl group, a hexyl group, a heptyl group, an octyl group, a nonyl group, and a decyl group. Preferred examples thereof include alkyl groups each having 1 to 8 carbon atoms, such as a methyl group, an ethyl group, a propyl group, a butyl group, a pentyl group, a hexyl group, a heptyl group, and an octyl group. The alkyl group may be linear or branched.

Specific examples of the cycloalkyl group include a cyclopropyl group, a cyclobutyl group, a cyclopentyl group, a cyclohexyl group, a cycloheptyl group, a cyclooctyl group, and a methylcyclohexyl group. Preferred examples thereof include a cyclopentyl group and a methylcyclohexyl group.

Specific examples of the aromatic hydrocarbon group or the aromatic heterocyclic group include a monovalent group produced by removing of one hydrogen atom from benzene, pentalene, indene, naphthalene, pyrrole, imidazole, pyrazole, thiazole, thiophene, pyridine, pyrazine, pyrimidine, pyridazine, triazine, isoindole, indazole, purine, isoquinoline, imidazole, naphthyridine, phthalazine, quinazoline, quinoxaline, cinnoline, quinoline, pteridine, perimidine, phenanthroline, phenazine, carboline, indole, carbazole, furan, benzofuran, isobenzofuran, oxanthrene, dibenzofuran, thiophene, thioxanthene, thianthrene, phenoxathiin, thionaphthene, isothianaphthene, thiophthene, thiophanthrene, or dibenzothiophene.

In the general formula (1) and the formula (1b), A represents an alkyl group having 1 to 10 carbon atoms, a cycloalkyl group having 3 to 11 carbon atoms, an aromatic hydrocarbon group having 6 to 30 carbon atoms, or an aromatic heterocyclic group having 3 to 30 carbon atoms, preferably an aromatic hydrocarbon group having 6 to 30 carbon atoms or an aromatic heterocyclic group having 3 to 30 carbon atoms, more preferably an aromatic hydrocarbon group having 6 to 18 carbon atoms or an aromatic heterocyclic group having 3 to 18 carbon atoms. In this case, the aromatic heterocyclic group is free of a fused heterocycle having 5 or more rings.

Specific examples of the alkyl group and the cycloalkyl group are the same as those of the alkyl group and the cycloalkyl group described for Y.

When A represents an aromatic hydrocarbon group or an aromatic heterocyclic group, specific examples thereof include a monovalent group produced by removing hydrogen from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxanthrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, benzisothiazole, or an aromatic compound in which a plurality of such aromatic rings are linked to each other. Preferred examples thereof include a monovalent group produced by removing hydrogen from benzene, naphthalene, anthracene, pyridine, pyrazine, pyrimidine, pyridazine, triazine, isoindole, indazole, purine, isoquinoline, imidazole, naphthyridine, phthalazine, quinazoline, benzodiazepine, quinoxaline, cinnoline, quinoline, pteridine, phenanthridine, acridine, perimidine, phenanthroline, phenazine, carboline, indole, carbazole, dibenzofuran, dibenzothiophene, or an aromatic compound in which a plurality of such aromatic rings are linked to each other.

It should be noted that in the case of the group produced from an aromatic compound in which a plurality of aromatic rings are linked to each other, the number of the aromatic rings to be linked to each other is preferably 2 to 10, more preferably 2 to 7, and the aromatic rings to be linked to each other may be identical to or different from each other. In that case, the bonding position of Z to be bonded to nitrogen is not limited, and Z may be bonded to a ring at a terminal portion of linked aromatic rings or may be bonded to a ring at the central portion thereof. Here, the term "aromatic ring" is a generic term for an aromatic hydrocarbon ring and an aromatic heterocycle. In addition, when the linked aromatic rings include at least one heterocycle, the linked aromatic rings are included in the category of the aromatic heterocycle.

Here, the monovalent group produced by the linking of a plurality of aromatic rings is, for example, represented by any one of the following formulae.

$$—Ar_1—Ar_2—Ar_3 \qquad (15)$$

$$—Ar_1—Ar_2—Ar_3 \quad \overset{Ar_4}{|} \quad (16)$$

$$—Ar_1—Ar_2—Ar_3 \quad \overset{Ar_4}{\underset{\underset{Ar_6}{|}}{\overset{|}{Ar_5}}} \quad (17)$$

In the formulae (15) to (17), $Ar_1$ to $Ar_6$ each represent a substituted or non-substituted aromatic ring.

Specific examples of the group produced by the linking of a plurality of aromatic rings include monovalent groups each produced by removing hydrogen from, for example, biphenyl, terphenyl, bipyridine, bipyrimidine, bitriazine, terpyridine, bistriazylbenzene, dicarbazolylbenzene, carbazolylbiphenyl, dicarbazolylbiphenyl, phenylterphenyl, carbazolylterphenyl, binaphthalene, phenylpyridine, phenylcarbazole, diphenylcarbazole, diphenylpyridine, phenylpyrimidine, diphenylpyrimidine, phenyltriazine, diphenyltriazine, phenylnaphthalene, or diphenylnaphthalene.

Here, the aromatic heterocyclic group is free of a fused heterocycle having 5 or more rings. When a fused heterocycle is included in the aromatic heterocyclic group, the fused heterocycle is limited to a fused aromatic heterocycle having up to 4 rings.

The aromatic hydrocarbon group or the aromatic heterocyclic group may have a substituent, and when any such group has a substituent, the substituent is an alkyl group having 1 to 20 carbon atoms, a cycloalkyl group having 3 to 20 carbon atoms, an alkoxy group having 1 to 2 carbon atoms, an acetyl group, a secondary amino group having 6 to 18 carbon atoms, a secondary phosphanyl group having 6 to 18 carbon atoms, or a silyl group having 3 to 18 carbon atoms. The substituent is preferably an alkyl group having 1 to 4 carbon atoms, a cycloalkyl group having 3 to 6 carbon atoms, or a secondary amino group having 6 to 15 carbon atoms.

When A represents an aromatic hydrocarbon group or an aromatic heterocyclic group, and the group has a substituent, the total number of substituents is 1 to 10. The number is preferably 1 to 6, more preferably 1 to 4. In addition, when the group has two or more substituents, the substituents may be identical to or different from each other.

In the general formula (1), at least one of Y and A represents an alkyl group or a cycloalkyl group. It is preferred that Y represent an alkyl group or a cycloalkyl group, and it is more preferred that two Y's each represent an alkyl group or a cycloalkyl group.

R's each independently represent hydrogen, an alkyl group having 1 to 10 carbon atoms, a cycloalkyl group having 3 to 11 carbon atoms, an aromatic hydrocarbon group having 6 to 12 carbon atoms, or an aromatic heterocyclic group having 3 to 12 carbon atoms. R's each preferably represent hydrogen, an alkyl group having 1 to 8 carbon atoms, a cycloalkyl group having 5 to 6 carbon atoms, an aromatic hydrocarbon group having 6 to 10 carbon atoms, or an aromatic heterocyclic group having 5 to 12 carbon atoms.

Specific examples of the alkyl group, the cycloalkyl group, the aromatic hydrocarbon group, or the aromatic heterocyclic group are identical to those of the alkyl group, cycloalkyl group, aromatic hydrocarbon group, or aromatic heterocyclic group constituting Y.

In the general formula (2), X's each independently represent nitrogen or methine and at least one of X's represents nitrogen.

In the general formula (2), Y's each independently represent hydrogen, an alkyl group having 1 to 10 carbon atoms, a cycloalkyl group having 3 to 11 carbon atoms, an aromatic hydrocarbon group having 6 to 12 carbon atoms, or an aromatic heterocyclic group having 3 to 12 carbon atoms. Y's each preferably represent an alkyl group having 1 to 10 carbon atoms or a cycloalkyl group having 3 to 11 carbon atoms.

Specific examples of the alkyl group, the cycloalkyl group, the aromatic hydrocarbon group, or the aromatic heterocyclic group are identical to those of the alkyl group, cycloalkyl group, aromatic hydrocarbon group, or aromatic heterocyclic group constituting Y.

In the formula (1b), A represents an aromatic hydrocarbon group having 6 to 30 carbon atoms or an aromatic heterocyclic group having 3 to 30 carbon atoms. A preferably represents an aromatic hydrocarbon group having 6 to 18 carbon atoms or an aromatic heterocyclic group having 3 to 18 carbon atoms. Here, the aromatic heterocyclic group is free of a fused heterocycle having 5 or more rings.

Specific examples of the aromatic hydrocarbon group or the aromatic heterocyclic group are identical to those of the aromatic hydrocarbon group or aromatic heterocyclic group constituting A.

In the general formulae (3) to (6), A's, Y's, R's, and X's each have the same meaning as that in the general formula (2).

The indolocarbazole compounds represented by the general formulae (1) to (6) can each be synthesized by employing a known approach after selecting a raw material in accordance with the structure of the target compound.

For example, a skeleton (IC-1) providing the indolocarbazole compound represented by the formula (3) can be synthesized by the following reaction formula with reference to a synthesis example described in Synlett, 2005, No. 1, p 42-48.

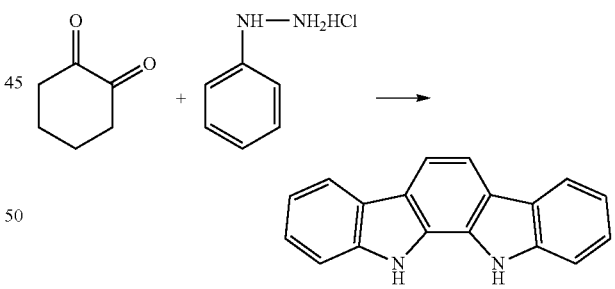

Further, a skeleton (IC-2) providing the indolocarbazole compound represented by the formula (4) can be synthesized by the following reaction formula with reference to a synthesis example described in Archiv der Pharmazie (Weinheim, Germany) 1987, 320(3), p 280-2.

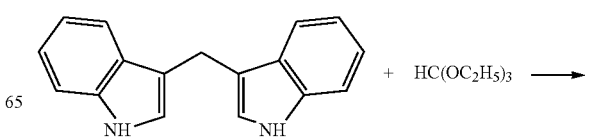

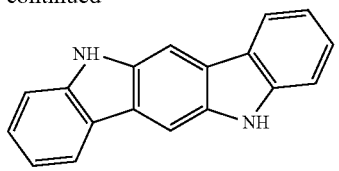

In addition, a skeleton (IC-3) providing each of the indolocarbazole compounds represented by the formulae (5) and (6) can be synthesized by the following reaction formula with reference to a synthesis example described in each of The Journal of Organic Chemistry, 2007, 72 (15) 5886, and Tetrahedron, 1999, 55, p 2371.

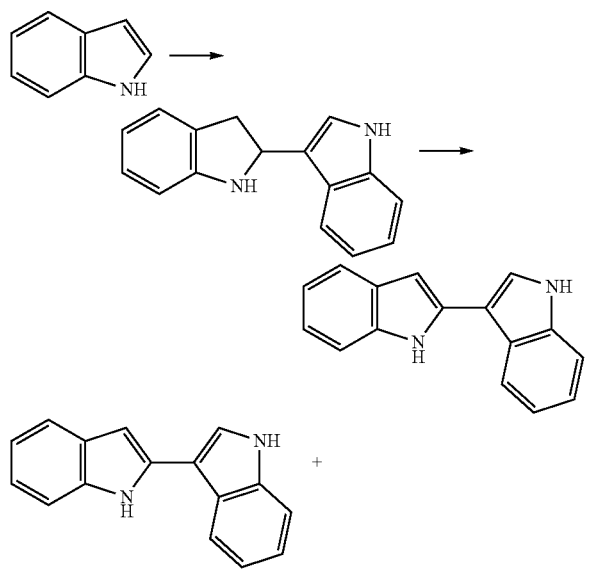

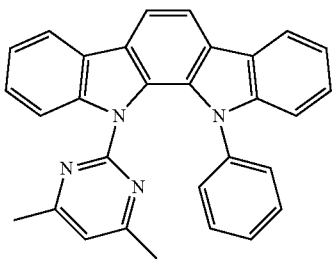

The compound represented by the general formula (1) can be synthesized by substituting hydrogen bonded to nitrogen of each of the indolocarbazole compounds obtained by the foregoing reaction formulae with the corresponding substituent through a coupling reaction such as the Ullmann reaction.

From another viewpoint, the compound represented by the general formula (1) is obtained by substituting the compound known to the public by Patent Literature 5 with an alkyl group. Accordingly, the compound can be synthesized by: forming the skeleton according to the synthesis method known to the public by Patent Literature 5; and substituting hydrogen bonded to nitrogen of the skeleton with an alkyl-substituted heterocyclic group such as an alkyl-substituted pyridyl. In addition, the compound can be synthesized by substituting the nitrogen-substituted heterocyclic group of the compound known to the public by Patent Literature 5 with an alkyl group.

Specific examples of the indolocarbazole compound represented by the general formula (1) are shown below. However, the material for an organic electroluminescent device of the present invention is not limited thereto.

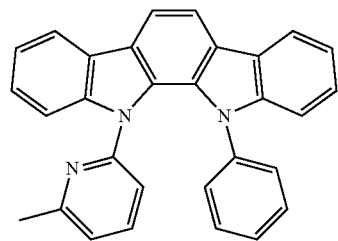
(1-1)

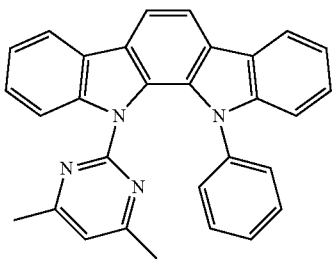
(1-2)

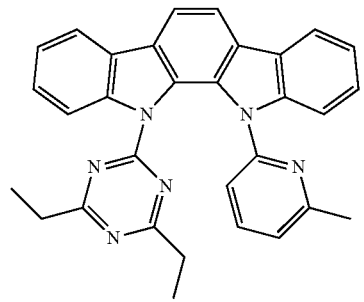
(1-3)

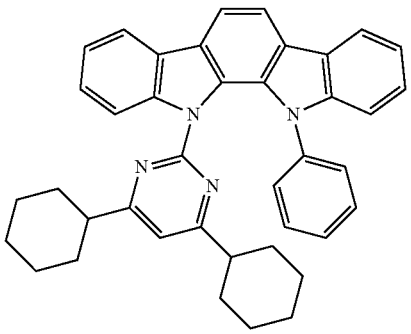
(1-4)

-continued
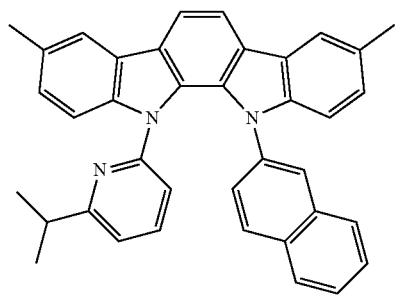
(1-5)
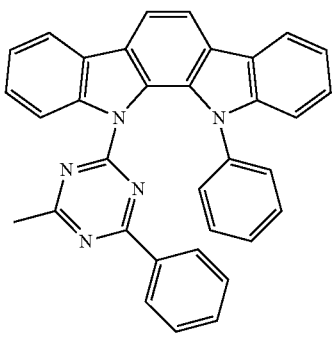
(1-6)
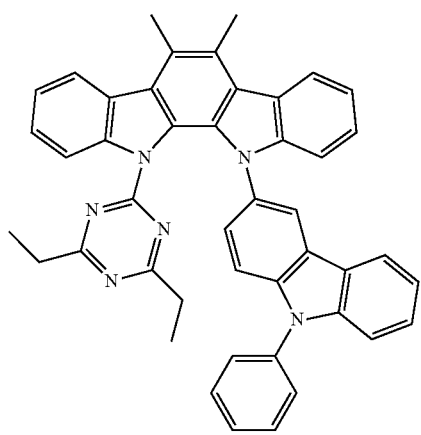
(1-7)
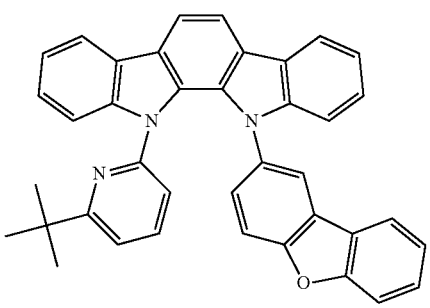
(1-8)
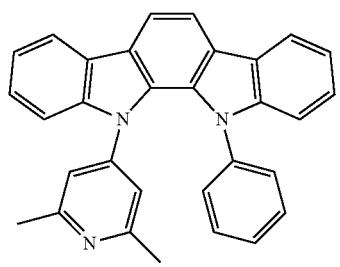
(1-9)
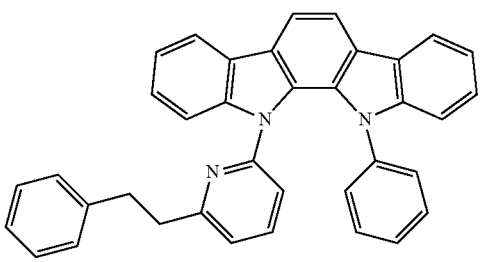
(1-10)
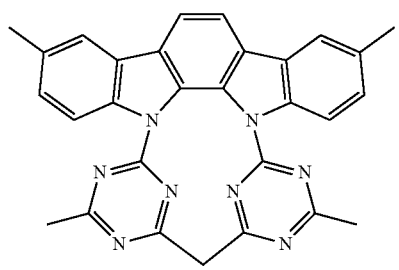
(1-11)
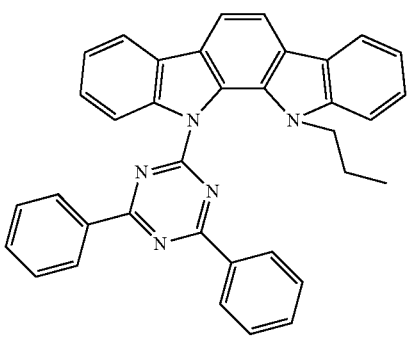
(1-12)

-continued
(1-13)
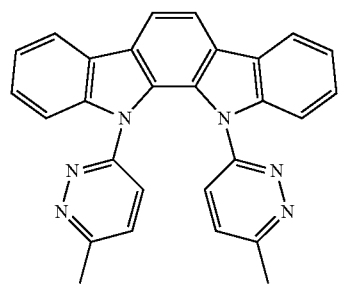
(1-14)
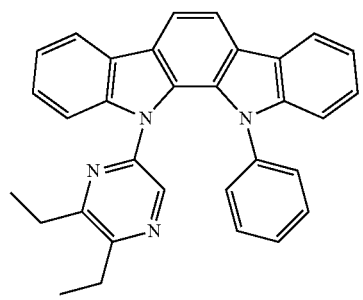
(1-15)
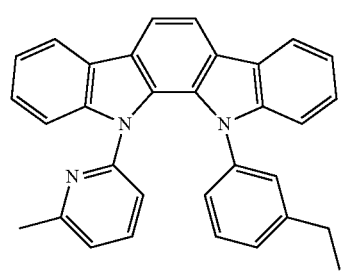
(2-1)
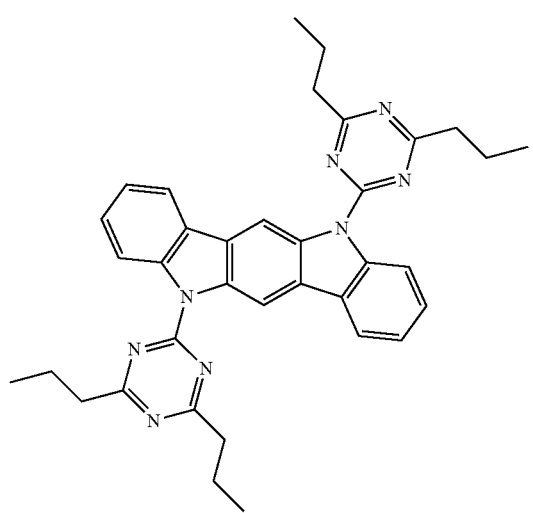
(2-2)
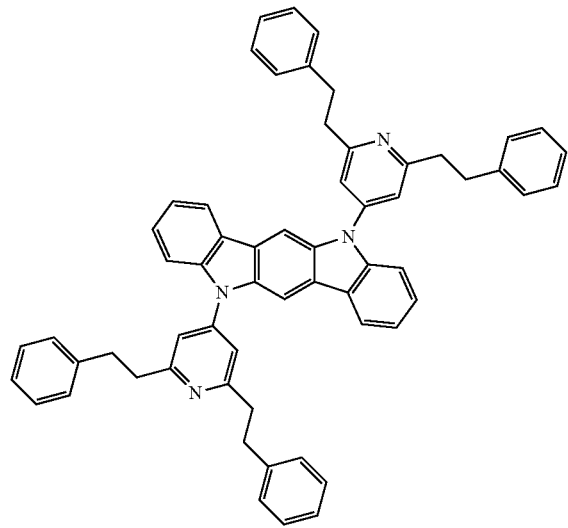
(2-3)
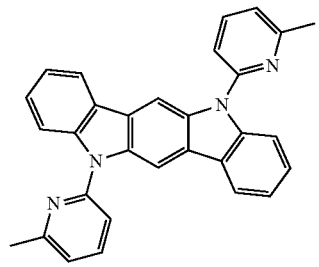

(2-4)
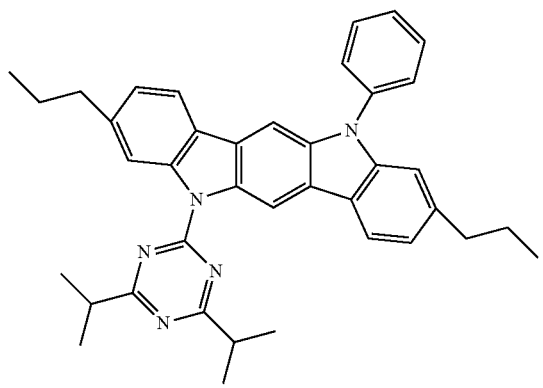
(2-5)
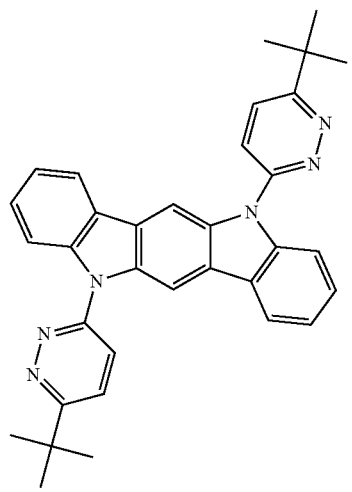
(2-6)
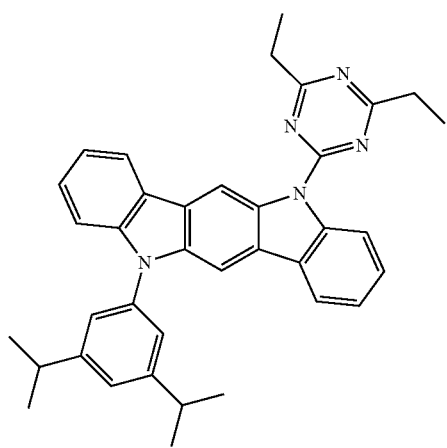
(3-1)
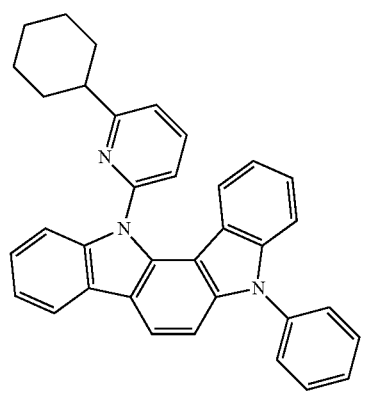
(3-2)
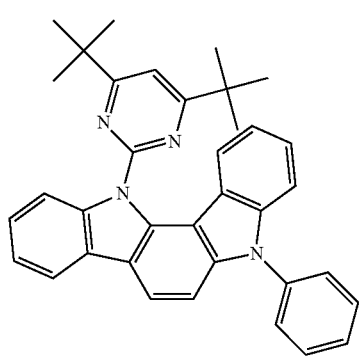
(3-3)
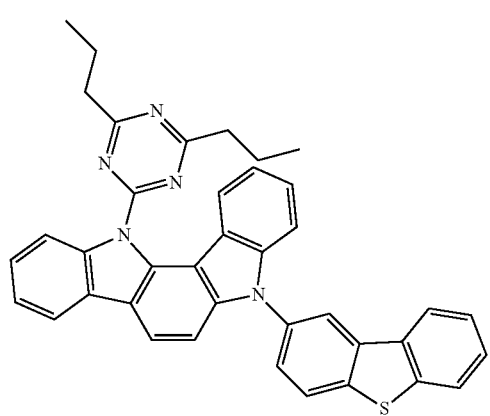

-continued
(3-4)
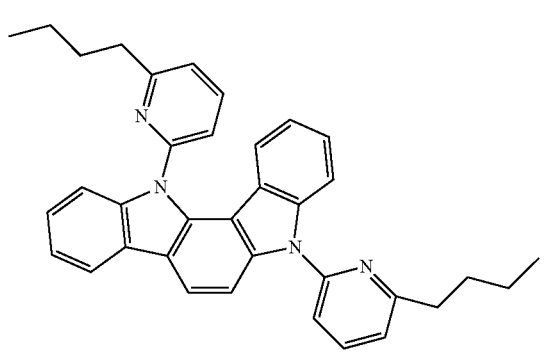
(3-5)
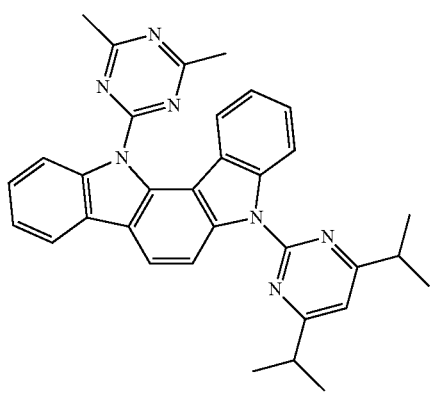
(3-6)
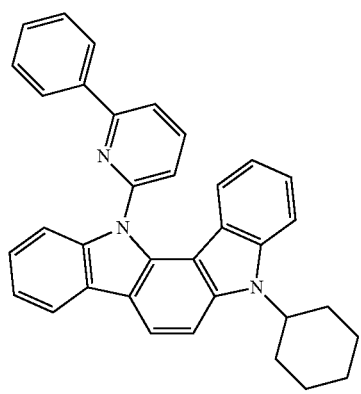
(3-7)
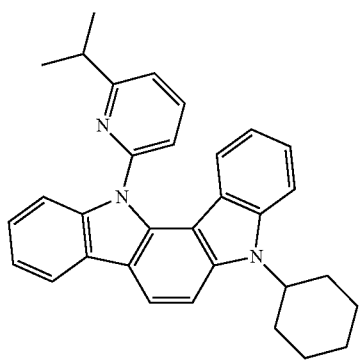
(3-8)
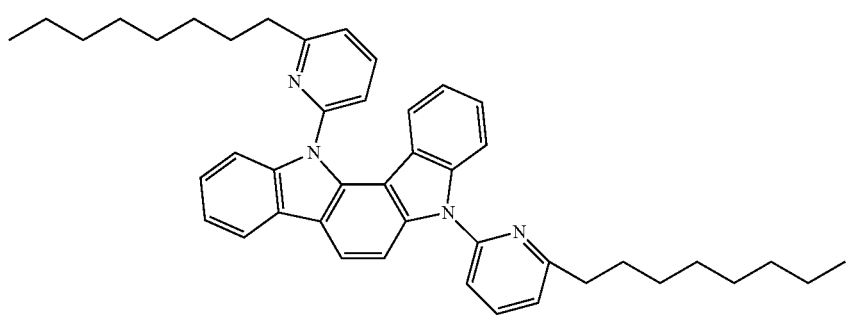
(3-9)
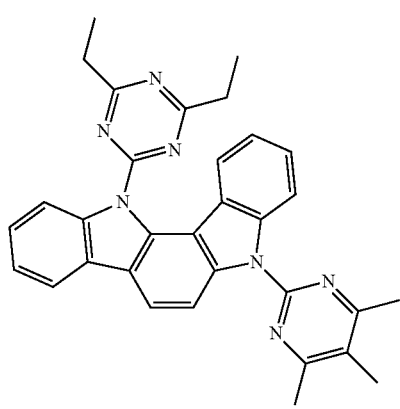
(3-10)
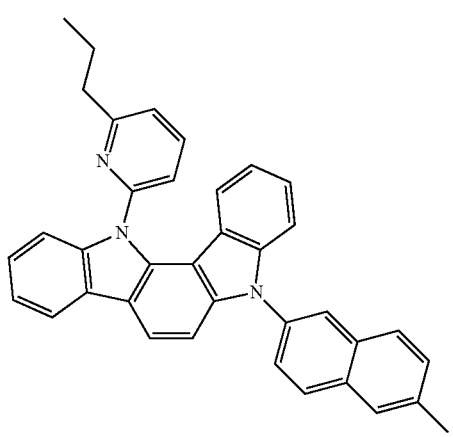

-continued
(3-11)
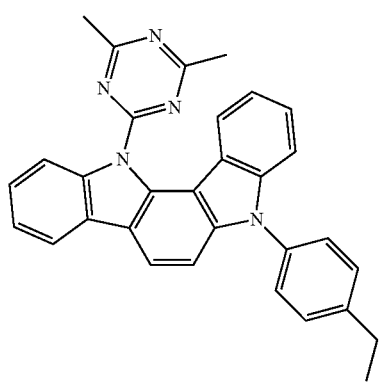
(4-1)
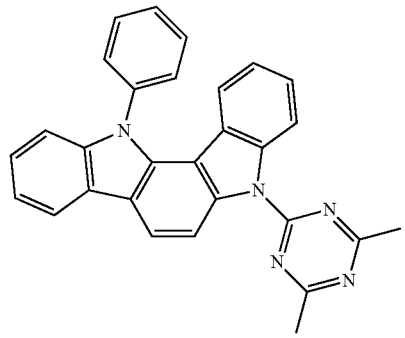
(4-2)
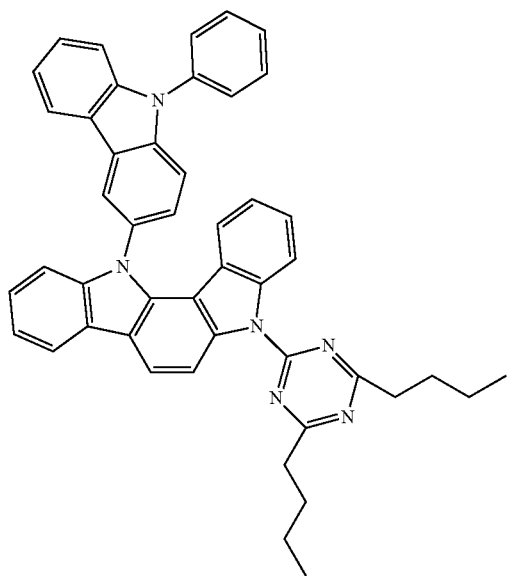
(4-3)
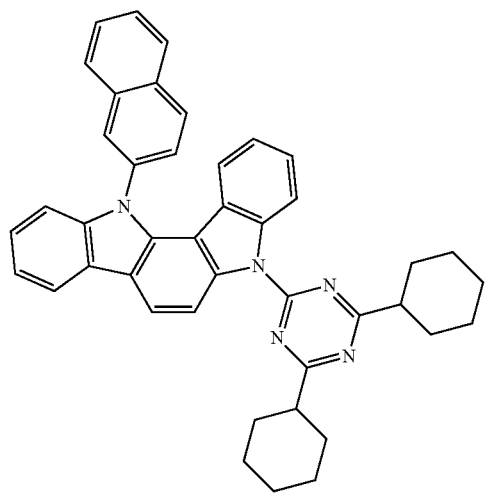
(4-4)
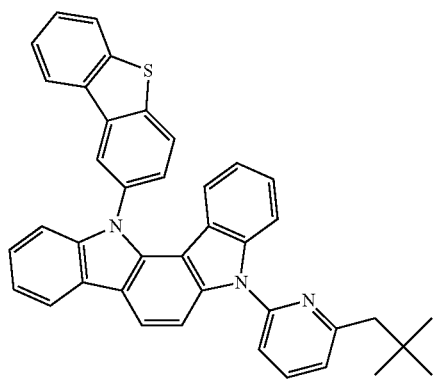
(4-5)
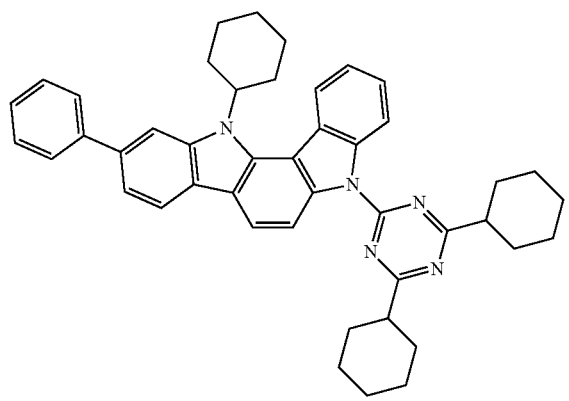

-continued
(5-1)
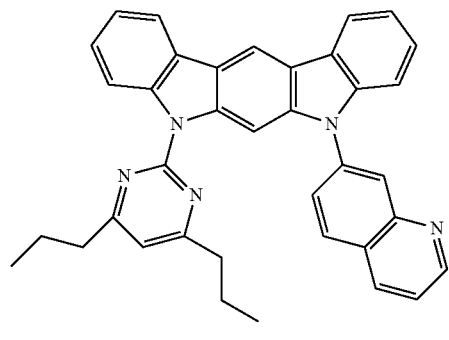
(5-2)
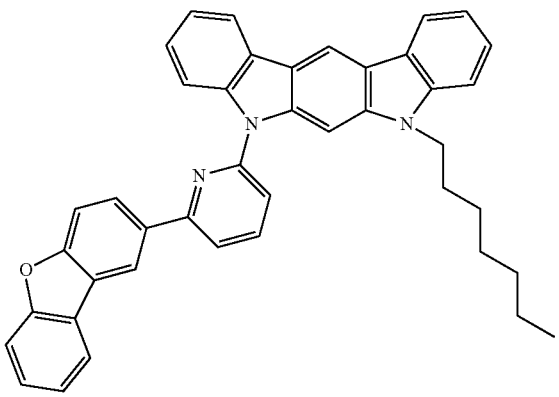
(5-3)
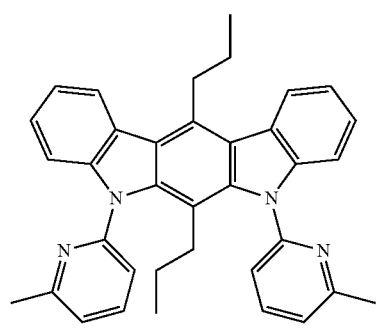
(5-4)
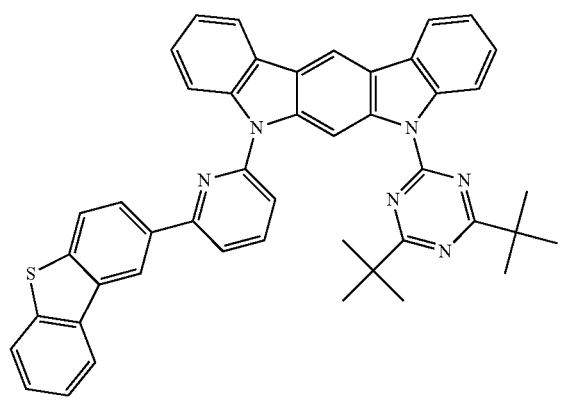
(5-5)
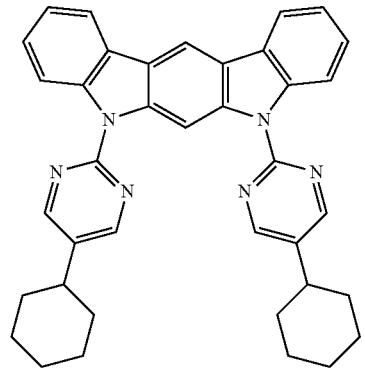
(5-6)
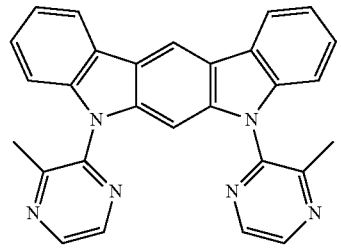
(6-1)
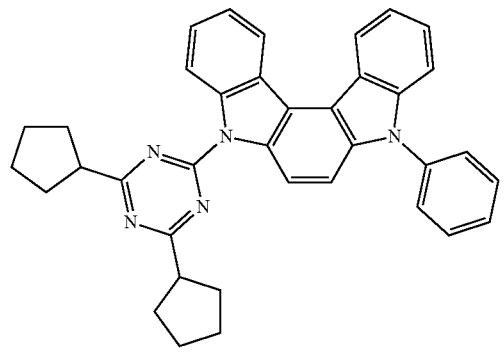
(6-2)
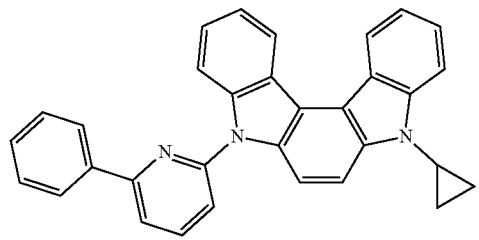

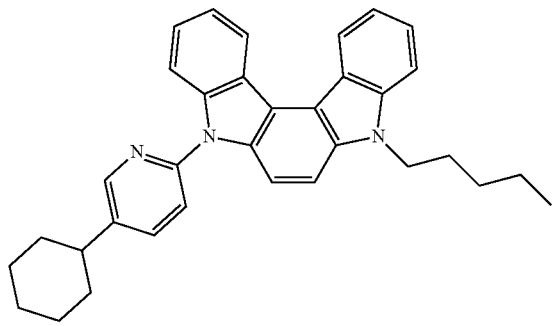

(6-3)

When the indolocarbazole compound represented by the general formula (1) is contained in at least one of a plurality of organic layers of an organic EL device formed by laminating an anode, the plurality of organic layers, and a cathode on a substrate, an excellent organic electroluminescent device is provided. A light-emitting layer, a hole-transporting layer, an electron-transporting layer, or a hole-blocking layer is suitable as the organic layer in which the indolocarbazole compound is contained. It is more preferred that the indolocarbazole compound be contained as a host material in a light-emitting layer containing a phosphorescent light-emitting dopant.

Next, the organic EL device of the present invention is described.

The organic EL device of the present invention has organic layers including at least one light-emitting layer between an anode and a cathode laminated on a substrate. In addition, at least one of the organic layers contains the indolocarbazole compound. The material for an organic electroluminescent device of the present invention is advantageously contained in the light-emitting layer together with a phosphorescent light-emitting dopant.

Next, the structure of the organic EL device of the present invention is described with reference to the drawings. However, the structure of the organic EL device of the present invention is by no means limited to one illustrated in the drawings.

FIG. 1 is a sectional view illustrating a structural example of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may have an exciton-blocking layer adjacent to the light-emitting layer, or may have an electron-blocking layer between the light-emitting layer and the hole-injecting layer. The exciton-blocking layer may be inserted on any of the anode side and the cathode side of the light-emitting layer, and may also be inserted simultaneously on both sides. The organic EL device of the present invention has the substrate, the anode, the light-emitting layer, and the cathode as its essential layers. The organic EL device of the present invention preferably has a hole-injecting/transporting layer and an electron-injecting/transporting layer in addition to the essential layers, and more preferably has a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure compared with FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated if necessary.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which may be used for manufacturing an amorphous, transparent conductive film. In order to produce the anode, it may be possible to form any of those electrode substances into a thin film by using a method such as vapor deposition or sputtering and form a pattern having a desired design thereon by photolithography. Alternatively, in the case of not requiring high pattern accuracy (about 100 μm or more), a pattern may be formed via a mask having a desired shape when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. Further, the sheet resistance as the anode is preferably several hundred Ω/□ or less. Further, the thickness of the resultant film is, depending on the material used, selected from usually the range of 10 to 1,000 nm, preferably the range of 10 to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode may be produced by forming any of those electrode substances into a thin film by using a method such as vapor deposition or sputtering. Further, the sheet resistance as the cathode is preferably several hundred Ω/□ or less, and the thickness of the resultant film is selected from usually the range of 10 nm to 5 μm, preferably the range of 50 to 200 nm. It should be noted that, in order for luminescence produced to pass through, any one of the anode and cathode of the organic EL device is preferably transparent or semi-transparent, because the light emission luminance improves.

Further, after any of the above-mentioned metals is formed into a film having a thickness of 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

Light-Emitting Layer

The light-emitting layer is a phosphorescent light-emitting layer, and contains a phosphorescent light-emitting dopant and a host material. It is recommended to use, as a material for the phosphorescent light-emitting dopant, a material containing an organic metal complex including at least one metal selected from ruthenium, rhodium, palladium, silver, rhenium, osmium, iridium, platinum, and gold. Such organic metal complexes are known in the prior art documents and the like, and a complex is selected therefrom and may be used.

Preferred examples of the phosphorescent light-emitting dopant include complexes such as Ir(ppy)$_3$, complexes such as (Bt)$_2$Iracac, and complexes such as (Btp)Ptacac, the complexes each having a noble metal element such as Ir as a central metal. Specific examples of those complexes are shown below, but the complexes are not limited to the compounds described below.

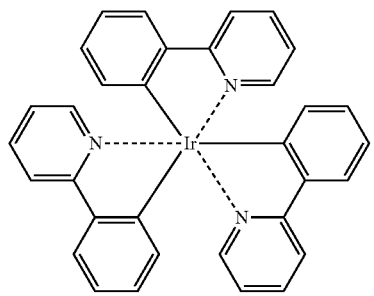

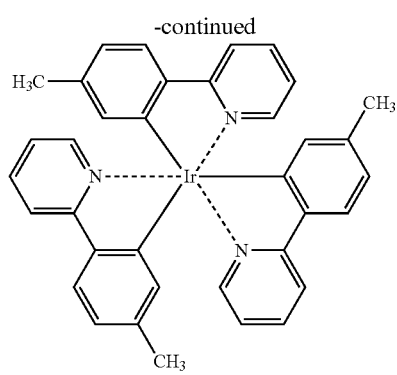

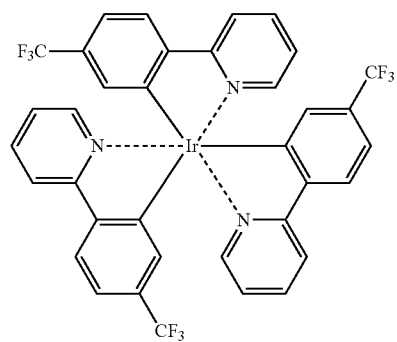

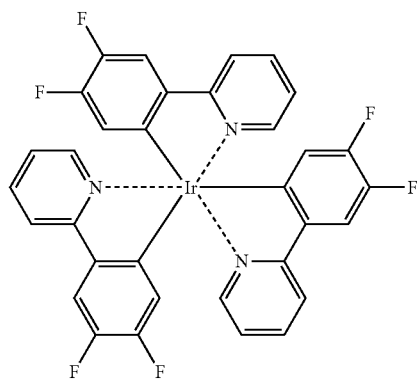

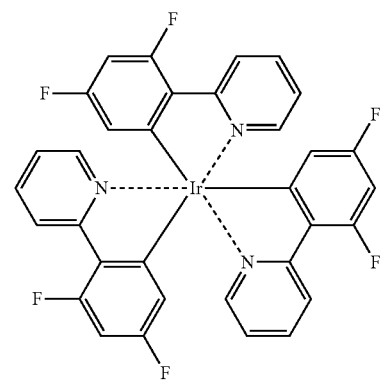

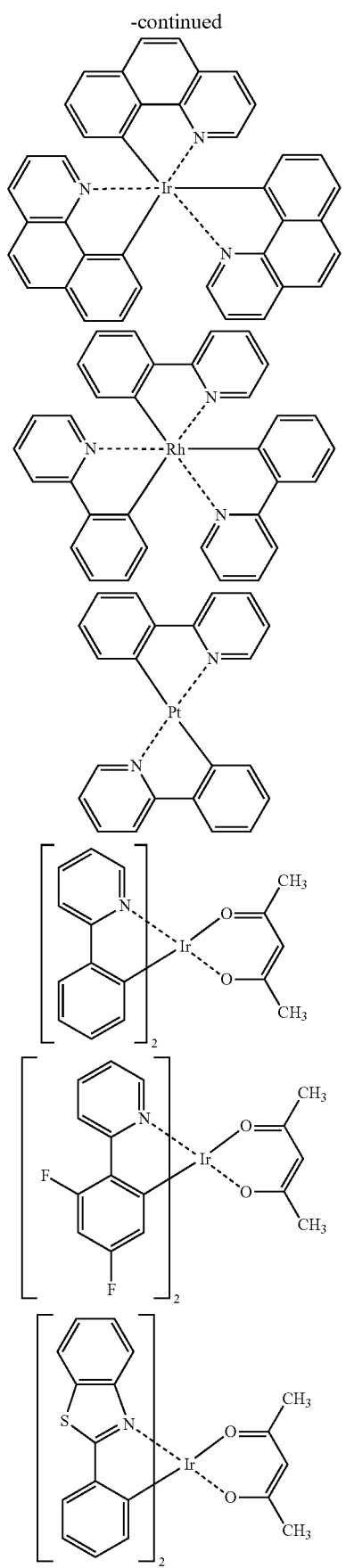
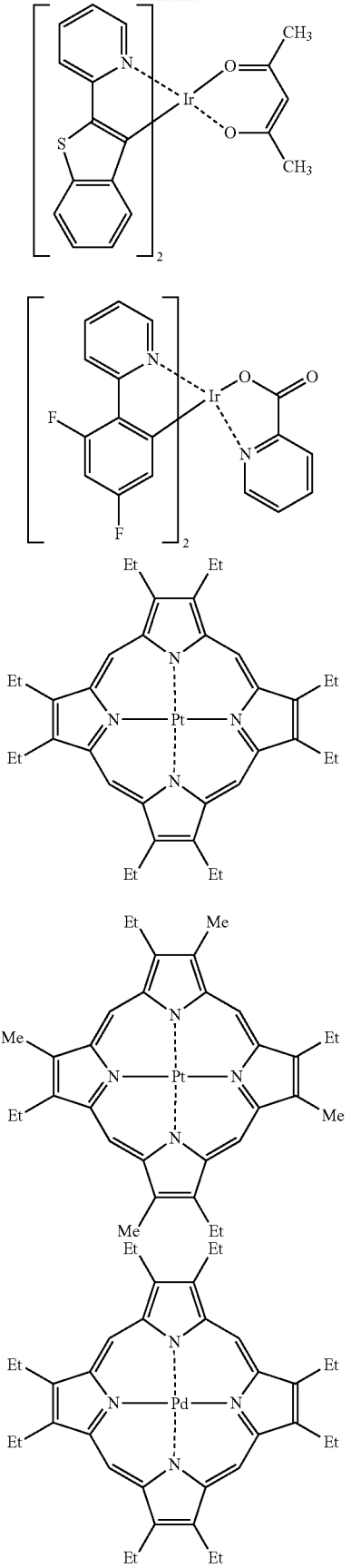

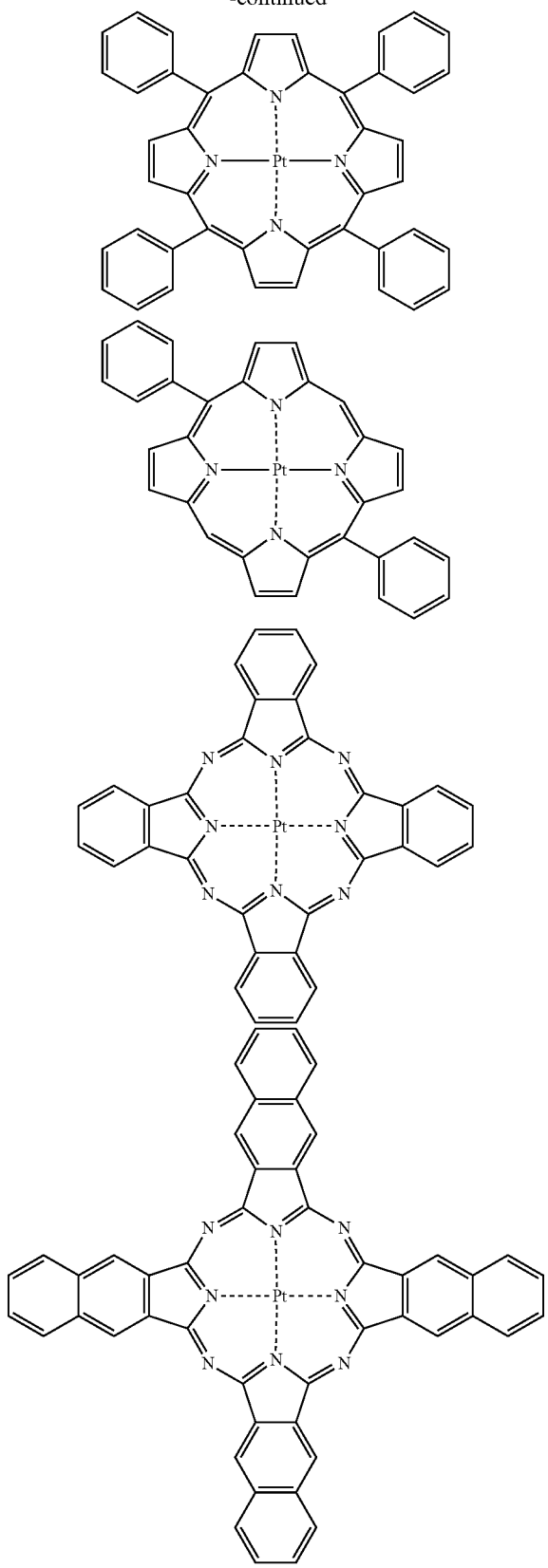

It is desirable that the content of the phosphorescent light-emitting dopant in the light-emitting layer be in the range of 2 to 40 wt %, preferably 5 to 30 wt %.

It is preferred to use, as a host material in the light-emitting layer, the indolocarbazole compound represented by the general formula (1). However, when the indolocarbazole compound is used in any of the organic layers other than the light-emitting layer, the material to be used in the light-emitting layer may be another host material other than the indolocarbazole compound, or the indolocarbazole compound and any other host material may be used in combination. Further, a plurality of kinds of known host materials may be used in combination.

It is preferred to use, as a usable known host compound, a compound that has a hole-transporting ability or an electron-transporting ability, is capable of preventing luminescence from having a longer wavelength, and has a high glass transition temperature.

Such other host materials are known because they are mentioned in many patent literatures and the like, and hence a suitable host material may be chosen from those in the patent literatures and the like. Specific examples of the host material, which are not particularly limited, include an indole derivative, a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrine-based compound, an anthraquinodimethane derivative, an anthrone derivative, a diphenylquinone derivative, a thiopyrane dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly(N-vinylcarbazole) derivative, an aniline-based copolymer, a thiophene oligomer, a polythiophene derivative, a polyphenylene derivative, a polyphenylenevinylene derivative, and a polyfluorene derivative.

—Injecting Layer—

The injecting layer refers to a layer provided between an electrode and an organic layer for the purpose of lowering a driving voltage and improving a light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be provided as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

It is preferred to use the indolocarbazole compound represented by the general formula (1) for the hole-blocking layer. However, when the indolocarbazole compound is used in any other organic layer, a known material for a hole-blocking layer may be used. Further, it is possible to use, as a material for the hole-blocking layer, any of the below-mentioned materials for the electron-transporting layer as required.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

Although the indolocarbazole compound represented by the general formula (1) according to the present invention can be used as a material for the electron-blocking layer, another material, i.e., any of the below-mentioned materials for the hole-transporting layer can be used as required. The thickness of the electron-blocking layer is preferably 3 to 100 nm, more preferably 5 to 30 nm.

—Exciton-Blocking Layer—

The exciton-blocking layer refers to a layer used for blocking excitons produced by the recombination of a hole and an electron in the light-emitting layer from diffusing in charge-transporting layers. Inserting this layer enables effective confinement of the excitons in the light-emitting layer, thereby being able to improve the luminous efficiency of the device. The exciton-blocking layer may be inserted on any of the anode side and the cathode side of the adjacent light-emitting layer, and may also be inserted simultaneously on both sides.

Although the indolocarbazole compound represented by the general formula (1) can be used as a material for the exciton-blocking layer, as other materials therefor, there are given, for example, 1,3-dicarbazolylbenzene (mCP) and bis(2-methyl-8-quinolinolato)-4-phenylphenolatoaluminum(III) (BAlq).

—Hole-Transporting Layer—

The hole-transporting layer is formed of a hole-transporting material having a function of transporting holes, and a single hole-transporting layer or a plurality of hole-transporting layers may be provided.

The hole-transporting material has hole-injecting property or hole-transporting property or has electron-blocking property, and any of an organic compound and an inorganic compound may be used as the hole-transporting material. Although it is preferred to use the indolocarbazole compound represented by the general formula (1) for the hole-transporting layer, any compound selected from conventionally known compounds may be used. Examples of the known hole-transporting material that may be used include a triazole derivative, an oxadiazole derivative, an imidazole derivative, a polyarylalkane derivative, a pyrazoline derivative, and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular weight oligomer, in particular, a thiophene oligomer. However, a porphyrin compound, an aromatic tertiary amine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers may be provided.

An electron-transporting material (which also serves as a hole-blocking material in some cases) has only to have a function of transferring electrons injected from the cathode into the light-emitting layer. Although it is preferred to use the material represented by the general formula (1) according to the present invention for the electron-transporting layer, any compound selected from conventionally known compounds may be used. Examples thereof include a nitro-substituted fluorene derivative, a diphenylquinone derivative, a thiopyran dioxide derivative, carbodiimide, a fluorenylidenemethane derivative, anthraquinodimethane, an anthrone derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative that has a quinoxaline ring known as an electron withdrawing group. Further, it is also possible to use a polymer material in which any of those materials is introduced in a polymer chain or is used as a polymer main chain.

EXAMPLES

Hereinafter, the present invention is described in more detail with reference to examples. It should be appreciated that the present invention is not limited to these examples and may be carried out in various forms as long as the various forms do not deviate from the gist of the present invention.

Example 1

Each thin film was laminated by a vacuum deposition method at a degree of vacuum of $4.0 \times 10^{-5}$ Pa on a glass substrate on which an anode formed of an ITO having a thickness of 110 nm had been formed. First, copper phthalocyanine (CuPC) was formed into a layer having a thickness of 25 nm on the ITO. Next, 4,4'-bis[N-(1-naphthyl)-N-phenylamino]biphenyl (NPB) was formed into a layer having a thickness of 40 nm to serve as a hole-transporting layer. Next, the compound (1-1) as a host material and tris(2-phenylpyridine)iridium (III) (Ir(ppy)$_3$) as a phosphorescent light-emitting dopant were co-deposited from different deposition sources onto the hole-transporting layer to form a light-emitting layer having a thickness of 40 nm. The concentration of Ir(ppy)$_3$ in the light-emitting layer was 10.0 wt %. Next, tris(8-hydroxyquinolinato)aluminum(III) (Alq3) was formed into a layer having a thickness of 20 nm to serve as an electron-transporting layer. Further, lithium fluoride (LiF) was formed into a layer having a thickness of 1.0 nm on the electron-transporting layer to serve as an electron-injecting layer. Finally, aluminum (Al) was formed into a layer having a thickness of 70 nm on the electron-injecting layer to serve as an electrode. Thus, an organic EL device was produced.

An external power source was connected to the resultant organic EL device to apply a DC voltage to the device. As a result, the device was observed to have such light-emitting characteristics as shown in Table 1. The columns "luminance," "voltage," and "luminous efficiency" in Table 1 show values at 10 mA/cm$^2$. It was found that the local maximum wavelength of the emission spectrum of the device was 520 nm and hence light emission from Ir(ppy)$_3$ was obtained.

Example 2

An organic EL device was produced in the same manner as in Example 1 except that the compound (1-2) was used as the host material for the light-emitting layer.

Example 3

An organic EL device was produced in the same manner as in Example 1 except that the compound (1-6) was used as the host material for the light-emitting layer.

Example 4

An organic EL device was produced in the same manner as in Example 1 except that the compound (1-8) was used as the host material for the light-emitting layer.

Example 5

An organic EL device was produced in the same manner as in Example 1 except that the compound (1-9) was used as the host material for the light-emitting layer.

Example 6

An organic EL device was produced in the same manner as in Example 1 except that the compound (2-3) was used as the host material for the light-emitting layer.

Example 7

An organic EL device was produced in the same manner as in Example 1 except that the compound (2-4) was used as the host material for the light-emitting layer.

Example 8

An organic EL device was produced in the same manner as in Example 1 except that the compound (3-1) was used as the host material for the light-emitting layer.

Example 9

An organic EL device was produced in the same manner as in Example 1 except that the compound (3-3) was used as the host material for the light-emitting layer.

Example 10

An organic EL device was produced in the same manner as in Example 1 except that the compound (3-6) was used as the host material for the light-emitting layer.

Example 11

An organic EL device was produced in the same manner as in Example 1 except that the compound (4-2) was used as the host material for the light-emitting layer.

Example 12

An organic EL device was produced in the same manner as in Example 1 except that the compound (4-3) was used as the host material for the light-emitting layer.

Comparative Example 1

An organic EL device was produced in the same manner as in Example 1 except that CBP was used as the host material for the light-emitting layer.

Comparative Example 2

An organic EL device was produced in the same manner as in Example 1 except that the following compound H-1 was used as the host material for the light-emitting layer.

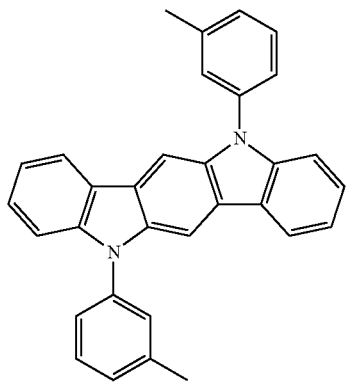

H-1

Comparative Example 3

An organic EL device was produced in the same manner as in Example 1 except that the following compound H-2 was used as the host material for the light-emitting layer.

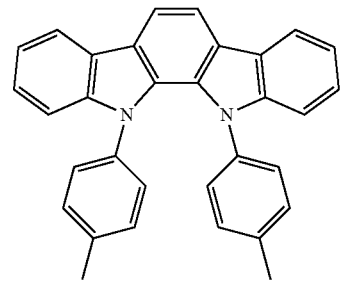

H-2

Comparative Example 4

An organic EL device was produced in the same manner as in Example 1 except that the following compound H-3 was used as the host material for the light-emitting layer.

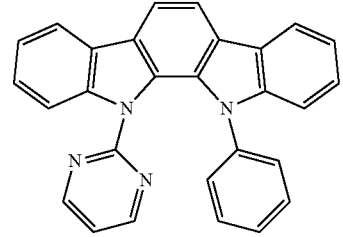

H-3

It was found that the local maximum wavelength of the emission spectrum each of the organic EL devices produced in Examples 2 to 12 and Comparative Examples 1 to 4 was 520 nm and hence light emission from Ir(ppy)$_3$ was obtained. Table 1 shows the compounds each used as the host material, light-emitting characteristics, and lifetime characteristics.

TABLE 1

|  | Compound | Luminance (cd/m$^2$) | Voltage (V) | Visual luminous efficiency (lm/W) |
|---|---|---|---|---|
| Example 1 | 1-1 | 2,890 | 7.0 | 13.0 |
| 2 | 1-2 | 2,820 | 7.0 | 12.7 |
| 3 | 1-6 | 2,850 | 6.3 | 14.2 |
| 4 | 1-8 | 2,920 | 7.1 | 12.9 |
| 5 | 1-9 | 2,850 | 7.1 | 12.6 |
| 6 | 2-3 | 2,820 | 6.5 | 13.6 |
| 7 | 2-4 | 2,820 | 7.0 | 12.7 |
| 8 | 3-1 | 2,810 | 7.2 | 12.3 |
| 9 | 3-3 | 2,950 | 6.8 | 13.6 |
| 10 | 3-6 | 2,980 | 6.9 | 13.6 |
| 11 | 4-2 | 2,880 | 7.0 | 12.9 |
| 12 | 4-3 | 2,810 | 6.6 | 13.4 |
| Comparative Example 1 | CBP | 2,420 | 9.3 | 8.2 |
| 2 | H-1 | 2,530 | 7.6 | 10.5 |
| 3 | H-2 | 2,470 | 7.8 | 9.9 |
| 4 | H-3 | 2,750 | 7.5 | 11.5 |

It is found from Table 1 that the organic EL device using the indolocarbazole compound represented by the general formula (1) shows good light-emitting characteristics as compared with the case where CBP generally known as a phosphorescent host is used. It is also found that the device shows good light-emitting characteristics as compared with the case where each of the H-1 and the H-2 as compounds each of which is free of an aromatic heterocyclic group in a molecule thereof is used. Further, it is found that the device shows good light-emitting characteristics as compared with the case where the H-3 free of an alkyl group in a molecule thereof is used. The superiority of the organic EL device using the indolocarbazole compound is apparent from the foregoing.

Example 13

A poly(3,4-ethylenedioxythiophene)/polystyrene sulfonate (PEDOT/PSS) (manufactured by H.C. Starck GmbH, trade name: CLEVIOS PCH8000) was formed into a film having a thickness of 25 nm by a spin coating method on a glass substrate on which an anode formed of an ITO having a thickness of 110 nm had been formed. Next, a light-emitting layer having a thickness of 40 nm was formed by the spin coating method with the compound (1-2) as a host material and a 1-wt % tetrahydrofuran (THF) solution prepared by adding 10.0 wt % of tris(2-phenylpyridine)iridium(III) (Ir(ppy)$_3$) as a phosphorescent light-emitting dopant with respect to the host material. Next, tris(8-hydroxyquinolinato) aluminum (III) (Alq3) was formed into a film having a thickness of 20 nm as an electron-transporting layer by a vacuum deposition method. Further, on the electron-transporting layer, lithium fluoride (LiF) was formed into a film having a thickness of 1.0 nm as an electron-injecting layer by the vacuum deposition method. Finally, on the electron-injecting layer, aluminum (Al) was formed into a thin film having a thickness of 70 nm as an electrode by the vacuum deposition method. Thus, an organic EL device was produced.

An external power source was connected to the resultant organic EL device, followed by application of a DC voltage. As a result, the organic EL device was found to have such light-emitting characteristics shown in Table 2. The column "current efficiency" in Table 2 shows values at 20 mA/cm$^2$. It was found that the local maximum wavelength of the emission spectrum of the device was 520 nm and hence light emission from Ir(ppy)$_3$ was obtained.

Example 14

An organic EL device was produced in the same manner as in Example 13 except that the compound (1-6) was used as the host material for the light-emitting layer.

Example 15

An organic EL device was produced in the same manner as in Example 13 except that the compound (1-12) was used as the host material for the light-emitting layer.

Example 16

An organic EL device was produced in the same manner as in Example 13 except that the compound (3-7) was used as the host material for the light-emitting layer.

Comparative Example 5

An organic EL device was produced in the same manner as in Example 13 except that the following compound H-2 was used as the host material for the light-emitting layer.

Comparative Example 6

An organic EL device was produced in the same manner as in Example 13 except that the following compound H-3 was used as the host material for the light-emitting layer.

It was found that the local maximum wavelength of the emission spectrum of each of the organic EL devices produced in Examples 14 to 16 and Comparative Examples 5 and 6 was 520 nm and hence light emission from Ir(ppy)$_3$ was obtained. Table 2 shows the compounds each used as the host material, light-emitting characteristics, and lifetime characteristics.

TABLE 2

|  | Compound | Current efficiency (Cd/A) |
|---|---|---|
| Example 13 | 1-2 | 17.8 |
| 14 | 1-6 | 20.2 |
| 15 | 1-12 | 15.7 |
| 16 | 3-7 | 16.2 |
| Comparative Example 5 | H-2 | 8.7 |
| 6 | H-3 | 9.2 |

It is found from Table 2 that the organic EL device using the indolocarbazole compound represented by the general formula (1) shows good light-emitting characteristics as compared with the case where the H-2 as a compound free of an aromatic heterocyclic group in a molecule thereof is used. In addition, the device shows good light-emitting characteristics as compared with the case where the H-3 as a compound free of an alkyl group in a molecule thereof is used. Accordingly, the superiority of the organic EL device using the indolocarbazole compound represented by the general formula (1) is apparent.

INDUSTRIAL APPLICABILITY

The indolocarbazole compound to be used in the organic electroluminescent device of the present invention is characterized in that nitrogen of the indolocarbazole skeleton is substituted with at least one nitrogen-containing six-membered ring, and that the compound has an alkyl group or a cycloalkyl group. The indolocarbazole compound may show good injecting/transporting properties for a hole and an electron, and have high durability. The voltage at which the organic EL device using the compound is driven is low. In particular, when the indolocarbazole compound is included in its light-emitting layer, the compound shows, for example, the following features. The compound improves a balance between both charges and hence increases the probability of their recombination. In addition, the compound has high energy in the lowest excited triplet state and hence can effectively suppress the transfer of triplet excitation energy from a dopant to a host material. Accordingly, the compound may impart excellent light-emitting characteristics. Moreover, the compound shows a good amorphous characteristic and high heat stability because the compound has the alkyl group or the cycloalkyl group. In addition, the compound is electrochemically stable. Accordingly, the compound may realize an organic EL device having a long driving lifetime and high durability. Further, the solubility of the compound improves because the compound has the alkyl group or the cycloalkyl group. Accordingly, the compound can be suitably applied not only to a dry process but also to a wet process, and hence may enable the production of devices by various film formation methods.

The organic EL device according to the present invention has practically satisfactory levels in light emission characteristics, driving lifetime, and durability. Thus, the organic EL device has a large technical value in applications to flat panel displays (display devices for portable phones, in-vehicle display devices, display devices for OA computers, televisions, and the like), light sources exerting characteristics of planar light emitters (light sources in lighting equipment and copiers and backlight sources in liquid crystal displays and instruments), sign boards, sign lamps, and the like.

The invention claimed is:

1. An organic electroluminescent device, comprising an anode, a plurality of organic layers including a phosphorescent light-emitting layer, and a cathode laminated on a substrate, wherein at least one organic layer selected from the group consisting of the phosphorescent light-emitting layer, a hole-transporting layer, an electron-transporting layer, and a hole-blocking layer contains an indolocarbazole compound represented by the following general formula (1):

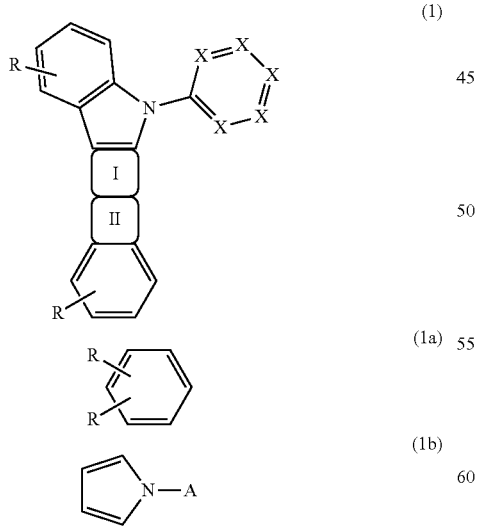

in the formula (1), a ring I represents an aromatic hydrocarbon ring represented by the formula (1a) that is fused to an adjacent ring at arbitrary positions, a ring II represents a heterocycle represented by the formula (1b) that is fused to an adjacent ring at arbitrary positions, X's each independently represent nitrogen or C—Y and 1 to 4 of X's represents nitrogen, and Y's each independently represent hydrogen, an alkyl group having 1 to 10 carbon atoms, or a cycloalkyl group having 3 to 11 carbon atoms, and at least one of Y's represents the alkyl group having 1 to 10 carbon atoms, or the cycloalkyl group having 3 to 11 carbon atoms, in the formula (1b), A represents an alkyl group having 1 to 10 carbon atoms, a cycloalkyl group having, 3 to 11 carbon atoms, or an aromatic hydrocarbon group having 6 to 30 carbon atoms, provided that at least one of Y and A represents an alkyl group having 1 to 10 carbon atoms or a cycloalkyl group having 3 to 11 carbon atoms, and in the general formula (1) and the formula (1a), R's each independently represent hydrogen, an alkyl group having 1 to 10 carbon atoms, a cycloalkyl group having 3 to 11 carbon atoms, an aromatic hydrocarbon group having 6 to 12 carbon atoms, or an aromatic heterocyclic group having 3 to 12 carbon atoms, wherein, when any of A and R's is an aromatic hydrocarbon group or an aromatic heterocyclic group, the aromatic hydrocarbon group or the aromatic heterocyclic group either has no substituent or has a substituent selected from an alkyl group having 1 to 20 carbon atoms, a cycloalkyl group having 3 to 20 carbon atoms, an alkoxy group having 1 to 2 carbon atoms, an acetyl group, a secondary amino group having 6 to 18 carbon atoms, a secondary phosphanyl group having 6 to 18 carbon atoms, or a silyl group having 3 to 18 carbon atoms.

2. An organic electroluminescent device according to claim 1, wherein the indolocarbazole compound represented by the general formula (1) is an indolocarbazole compound represented by the following general formula (2):

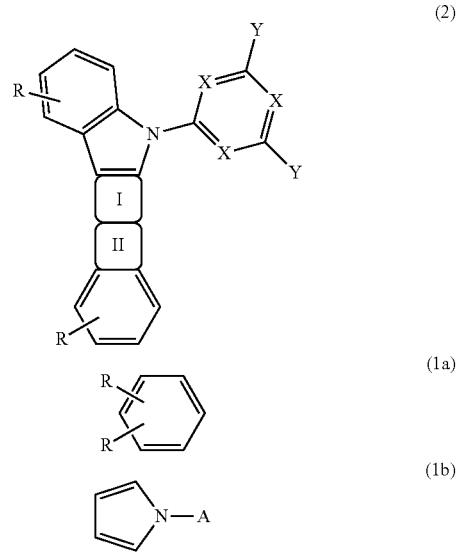

wherein, a ring I, a ring II, A, Y's, and R's have the same meanings as those in the general formula (1); and X's each independently represent nitrogen or CH and at least one of X's represents nitrogen.

3. An organic electroluminescent device according to claim 2, wherein the indolocarbazole compound represented by the general formula (2) is an indolocarbazole compound represented by any one of the following general formulae (3) to (6):

(3)

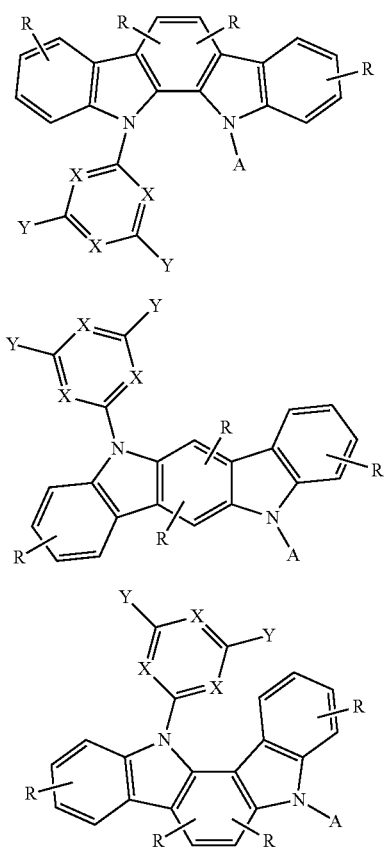

(4)

(5)

-continued (6)

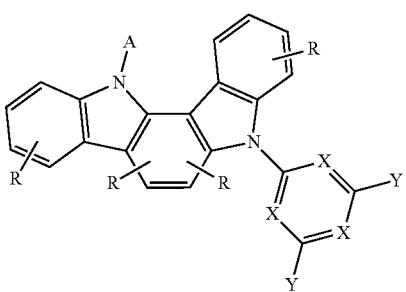

in the general formulae (3) to (6), A's, R's, X's and Y's have the same meanings as those in the general formula (2).

4. An organic electroluminescent device according to claim 1, wherein the organic layer containing the indolocarbazole compound comprises a light-emitting layer containing a phosphorescent light-emitting dopant.

5. An organic electroluminescent device according to claim 2, wherein the organic layer containing, the indolocarbazole compound comprises a light-emitting layer containing a phosphorescent light-emitting dopant.

6. An organic electroluminescent device according to claim 3, Wherein the organic layer containing the indolocarbazole compound comprises a light-emitting layer containing a phosphorescent light-emitting dopant.

* * * * *